(12) United States Patent
Abdou

(10) Patent No.: US 8,303,629 B1
(45) Date of Patent: Nov. 6, 2012

(54) SPINOUS PROCESS FUSION AND ORTHOPEDIC IMPLANTS AND METHODS

(76) Inventor: M. Samy Abdou, San Diego, CA (US)

(*) Notice: Subject to any disclaimer, the term of this patent is extended or adjusted under 35 U.S.C. 154(b) by 130 days.

(21) Appl. No.: 12/727,641

(22) Filed: Mar. 19, 2010

Related U.S. Application Data

(60) Provisional application No. 61/210,581, filed on Mar. 19, 2009.

(51) Int. Cl.
*A61B 17/70* (2006.01)
(52) U.S. Cl. .................................................. 606/248
(58) Field of Classification Search .......... 606/246–249, 606/277, 280–299
See application file for complete search history.

(56) References Cited

U.S. PATENT DOCUMENTS

| 4,554,914 | A  | * | 11/1985 | Kapp et al. ............... 606/86 A |
| 6,312,431 | B1 | * | 11/2001 | Asfora ........................ 606/279 |
| 7,048,736 | B2 | * | 5/2006  | Robinson et al. .......... 606/86 B |
| 7,727,233 | B2 | * | 6/2010  | Blackwell et al. .......... 606/71 |
| 7,871,426 | B2 | * | 1/2011  | Chin et al. ................. 606/248 |
| 2003/0040746 | A1 | * | 2/2003 | Mitchell et al. ............ 606/61 |
| 2007/0270812 | A1 | * | 11/2007 | Peckham .................... 606/61 |

* cited by examiner

*Primary Examiner* — Alvin Stewart
*Assistant Examiner* — Steven Cotroneo
(74) *Attorney, Agent, or Firm* — Gazdzinski & Associates, PC

(57) ABSTRACT

A spinal implant device immobilizes an attached vertebrae through a minimally invasive surgical approach while providing a compartment within the implant for the placement of bone graft or bone graft substitute. The bone graft material fuses the spinous processes and/or lamina portion of bone of the vertebral bone to which the device is attached.

21 Claims, 21 Drawing Sheets

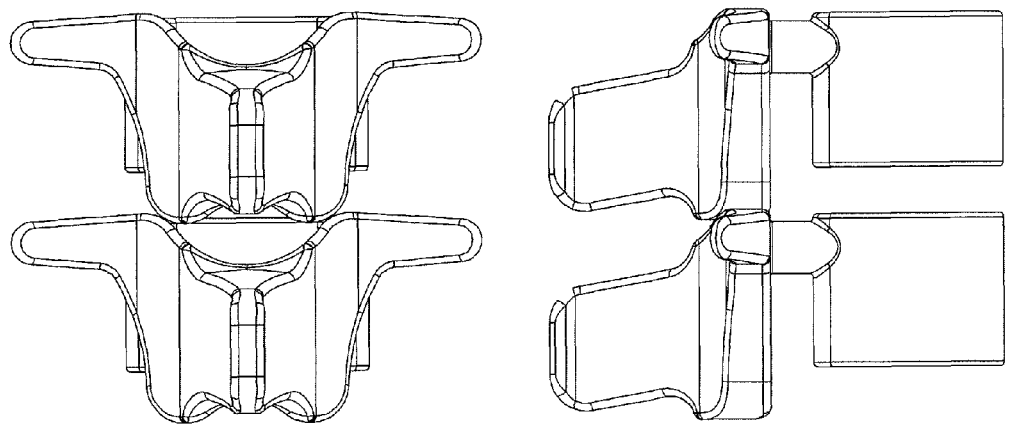
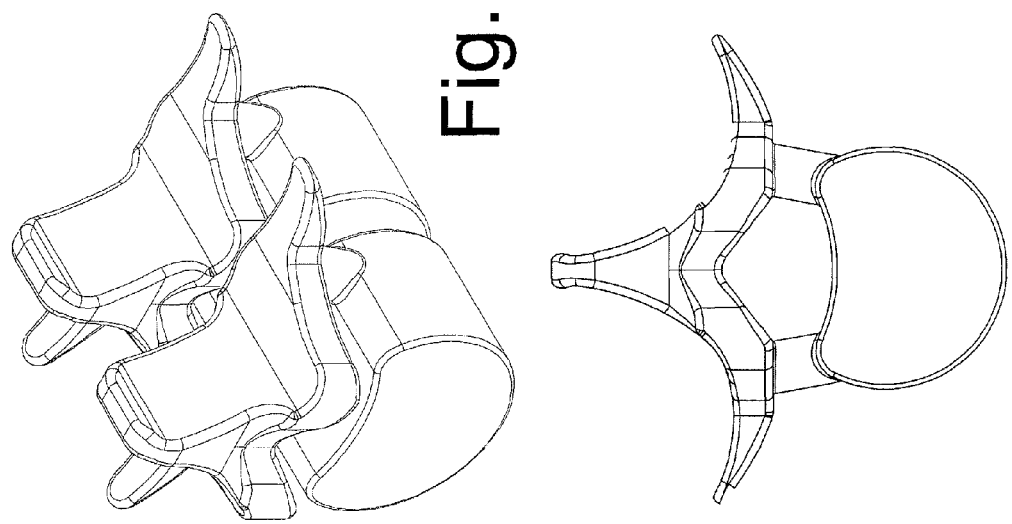
Fig. 1

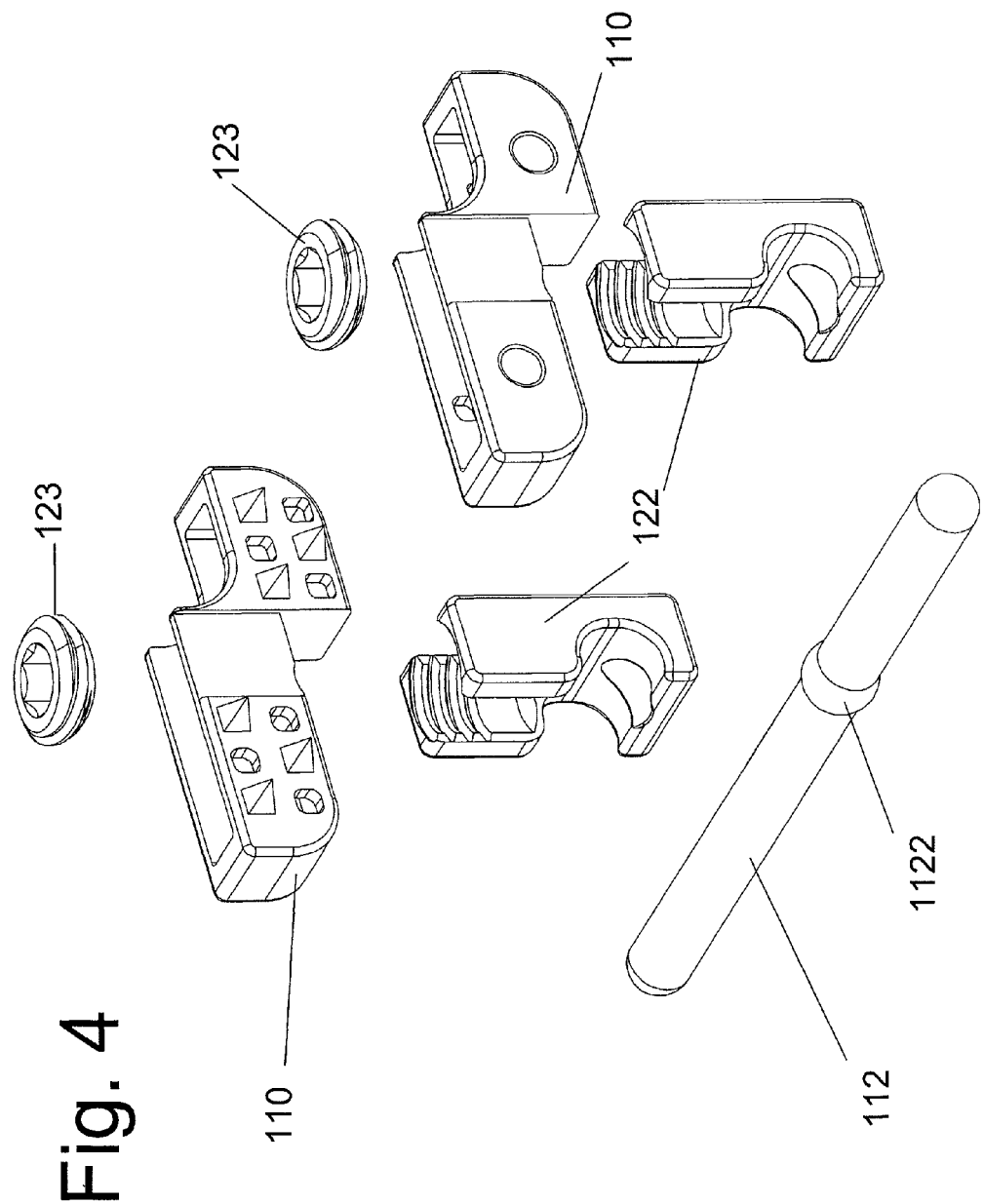

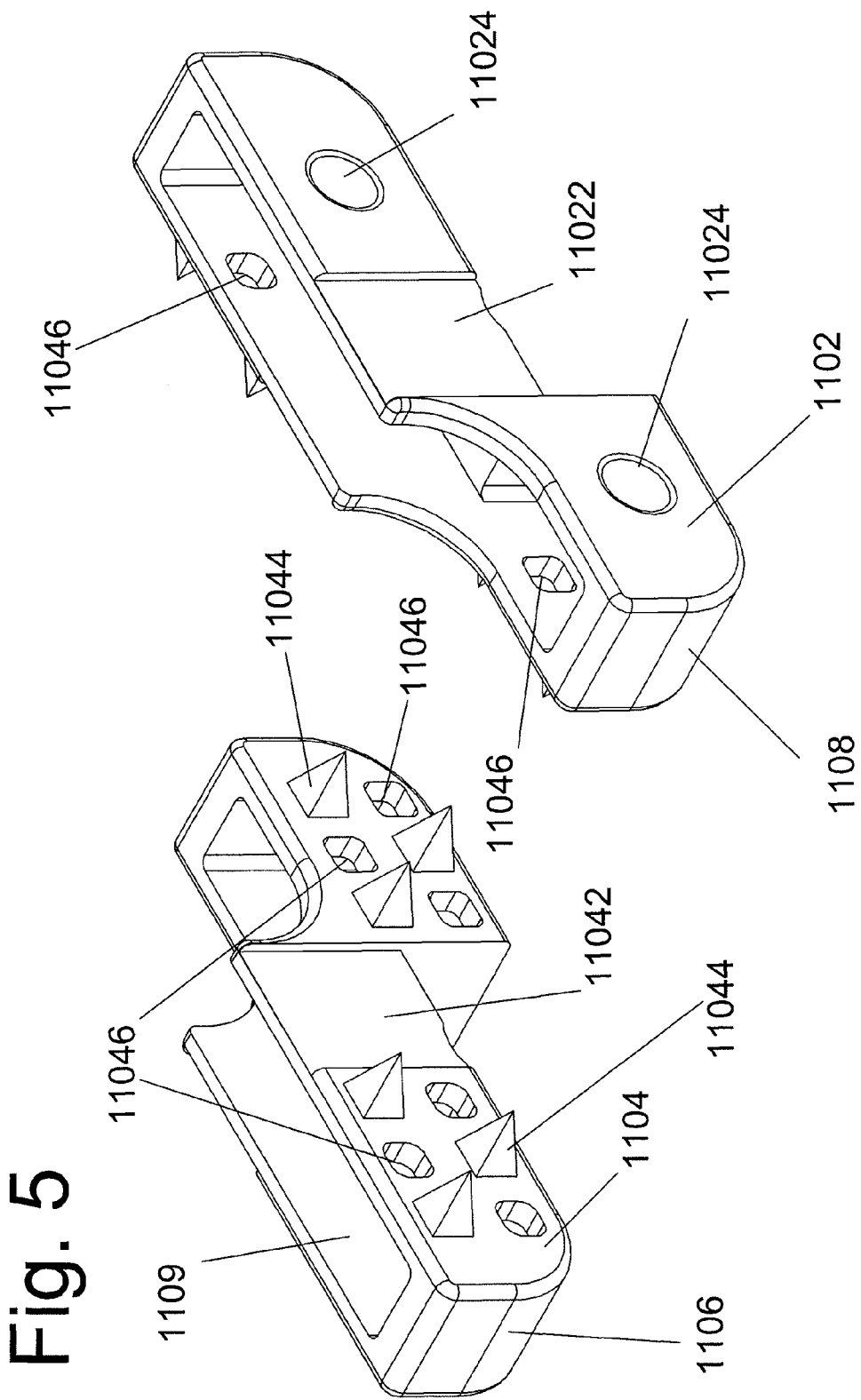

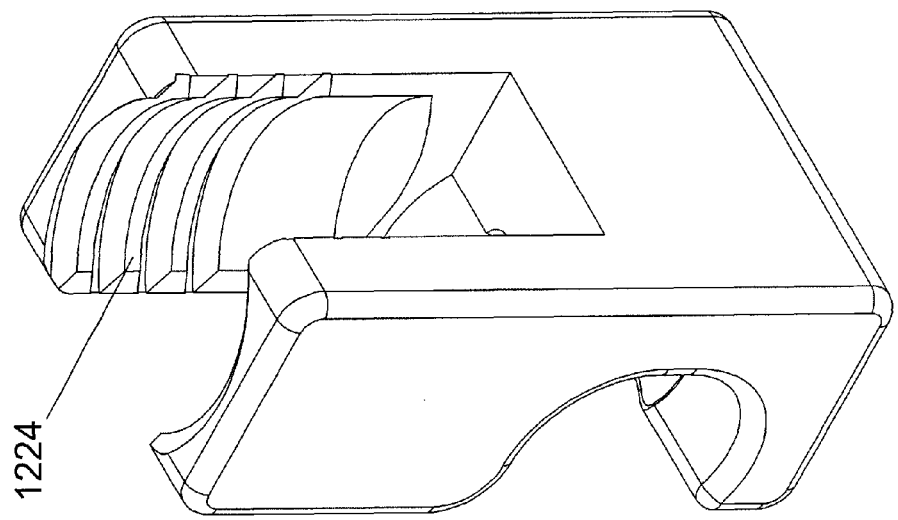
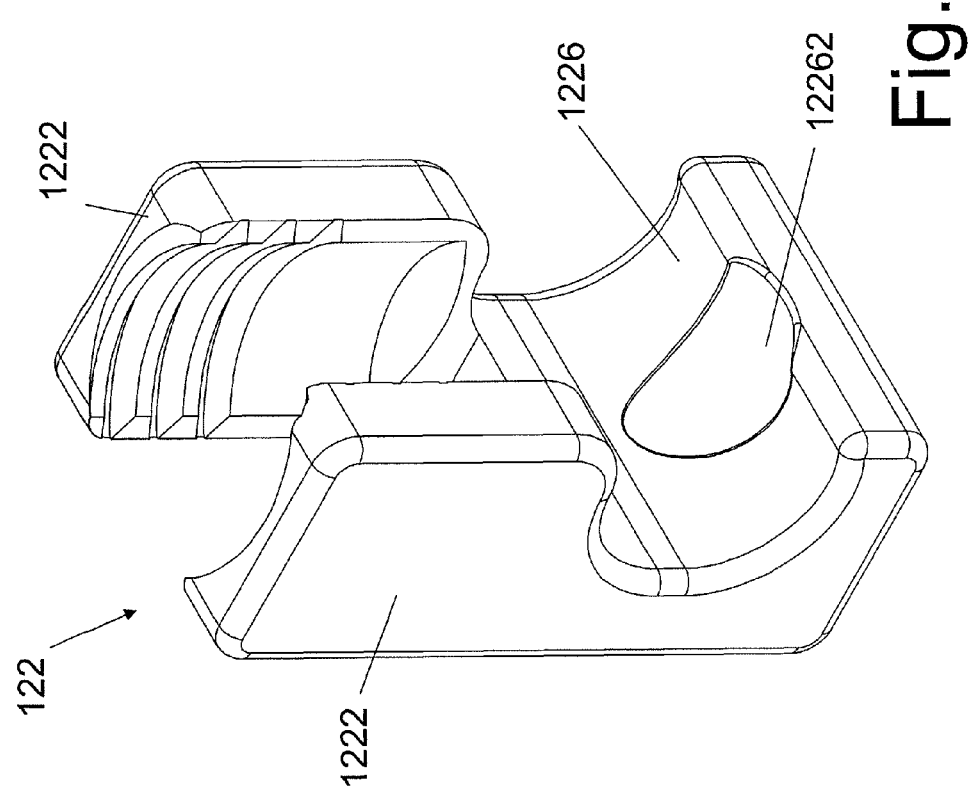
Fig. 7

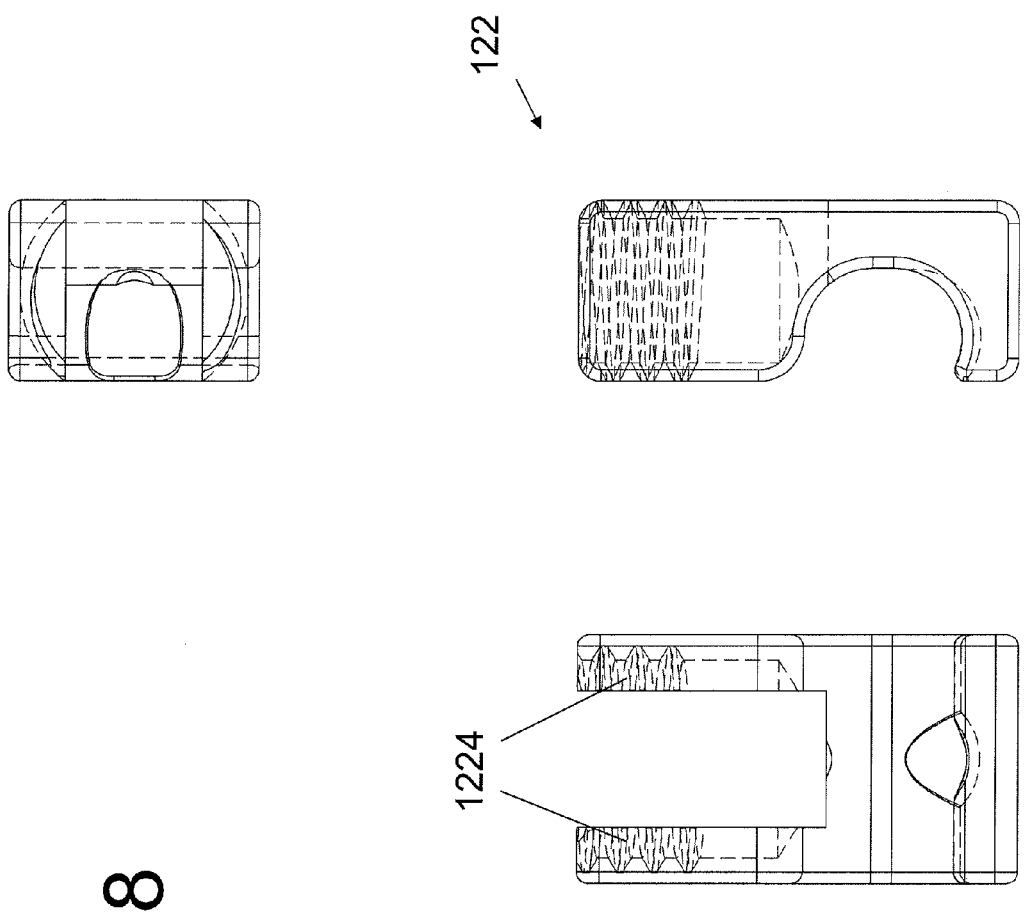

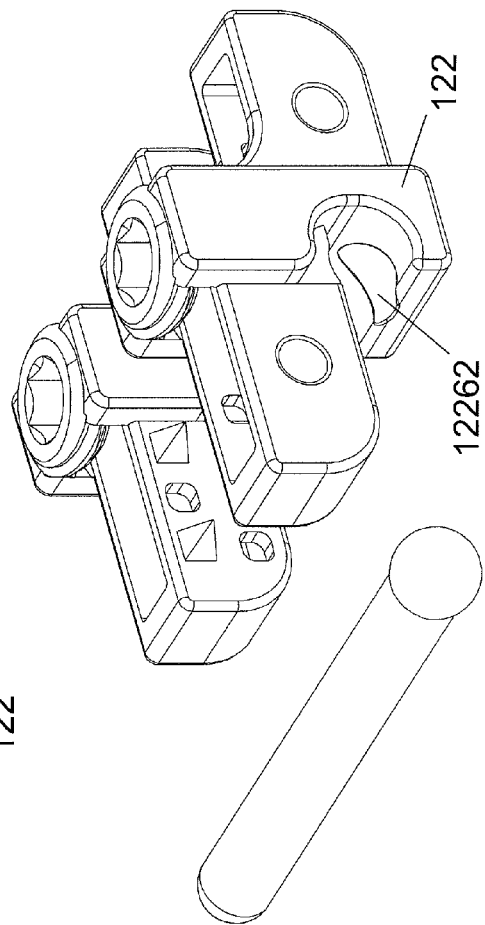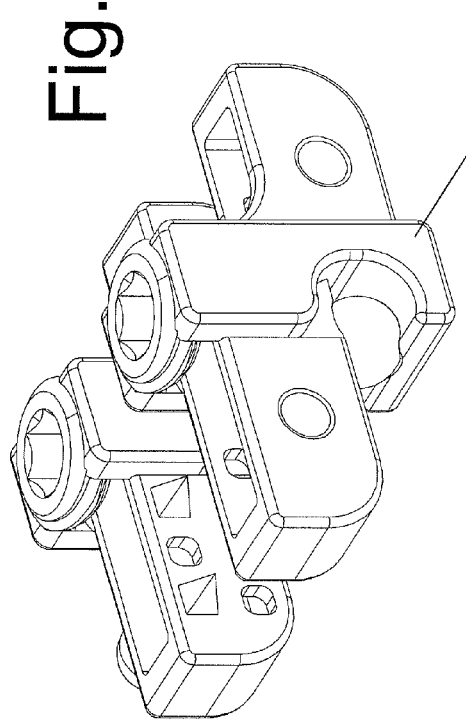

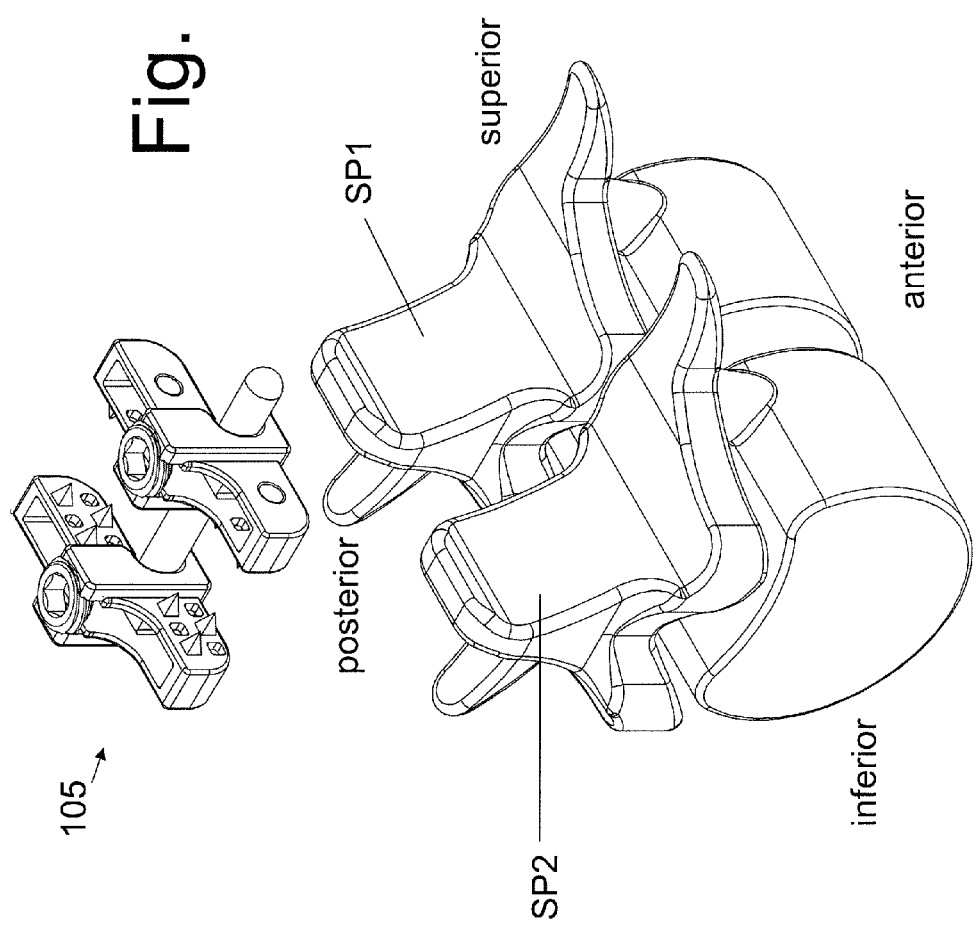

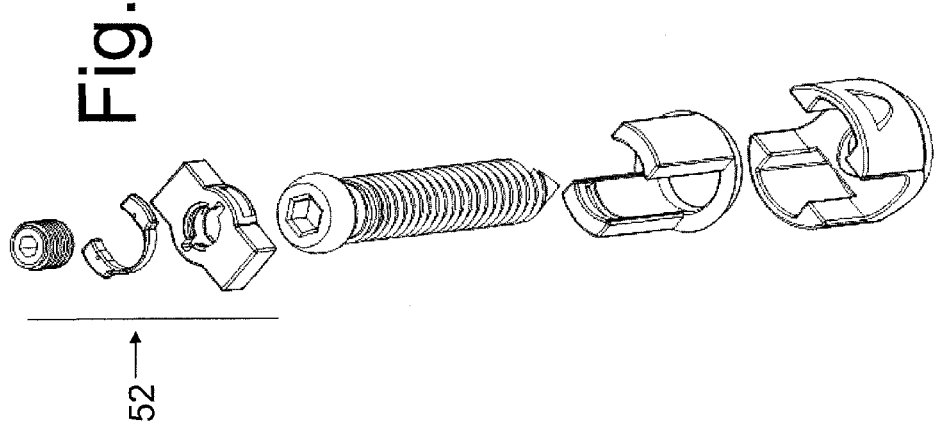
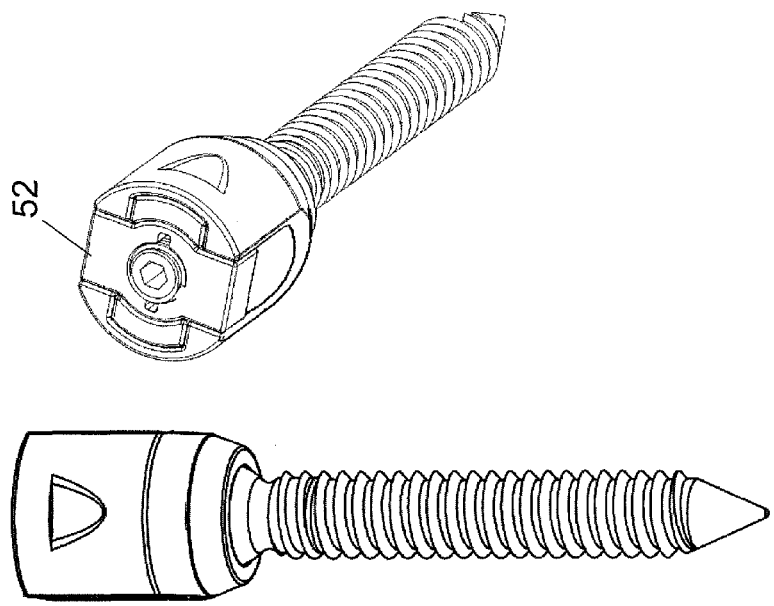

SPINOUS PROCESS FUSION AND ORTHOPEDIC IMPLANTS AND METHODS

REFERENCE TO PRIORITY DOCUMENT

This application claims priority of co-pending U.S. Provisional Patent Application Ser. No. 61/210,581 filed Mar. 19, 2009. Priority of the aforementioned filing date is hereby claimed and the disclosure of the Provisional Patent Application is hereby incorporated by reference in its entirety.

BACKGROUND

The present disclosure relates to devices and methods that permit fixation and stabilization of the bony elements of the skeleton of a patient. The devices permit adjustment and maintenance of the spatial relationship(s) between neighboring bones. Depending on the specifics of the embodiment design, the motion between adjacent skeletal segments may be limited or completely eliminated.

Spinal degeneration is an unavoidable consequence of aging and the disability produced by the aging spine has emerged as a major health problem in the industrialized world. Alterations in the anatomical alignment and physiologic motion that normally exists between adjacent spinal vertebrae can cause significant pain, deformity, weakness, and catastrophic neurological dysfunction.

Surgical decompression of the neural tissues and immobilization of the vertebral bones is a common option for the treatment of spinal disease. Currently, vertebral fixation is most frequently accomplished by anchoring bone screws into the pedicle portion of each vertebral body and then connecting the various screw fasteners with an interconnecting rod. Subsequent rigid immobilization of the screw/rod construct produces rigid fixation of the attached bones.

A shortcoming of the traditional rod/screw implant is the large surgical dissection required to provide adequate exposure for instrumentation placement. The size of the dissection site produces unintended damage to the muscle layers and otherwise healthy tissues that surround the diseased spine. A less invasive spinal fixation implant would advantageously minimize the damage produced by the surgical exposure of the spine.

In U.S. Pat. No. 7,048,736, Robinson et al teach the use of interspinous process plate to fixate adjacent vertebrae. As disclosed, the device is used to supplement orthopedic implant and/or bone graft material placed into the intervertebral disc between the attached vertebra. Thus the device functions to immobilize the vertebrae until bone fusion occurs but, in itself, does not provide a compartment for bone graft placement within the posterior aspect of the spine. Since bone graft material must be placed in order to achieve vertebral fusion, the device must be used in conjunction with bone graft material that is placed at a secondary site of the attached vertebra bones, such as within the disc space, between adjacent transverse processes, and the like. This is a significant disadvantage and prevents use of the Robinson device by itself to both immobilize and fuse the vertebral bones.

The growing experience with spinal fusion has shed light on the long-term consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The rigidity of the spinal fixation method has been shown to correlate with the rate of the degenerative progression of the adjacent segments. In specific, implantation of stiffer instrumentation, such as rod/screw implants, produced a more rapid progression of the degeneration disease at the adjacent segment than use of a less stiff fixation implant.

SUMMARY

This application discloses several exemplary devices that attach onto the spinous processes of adjacent vertebrae and address the limitation and shortcomings of prior devices and methods. In one embodiment, a device comprises an implant immobilizes the attached vertebrae through a minimally invasive surgical approach while providing a compartment within the implant for the placement of bone graft or bone graft substitute. The bone graft material then fuses the spinous processes and/or lamina portion of bone of the vertebral bone to which the device is attached. In another embodiment, the implant permits movement of the attached bone within a defined range of motion. The device is capable of preventing aberrant anterior and/or posterior spondylolisthesis as well as limiting the extent of flexion, extension, lateral flexion and rotation of the attached vertebral. Spinous process fixation provides good segmental immobilization through a minimally invasive surgical approach.

In other exemplary embodiments, the implant is anchored to the pedicle portion of at least one vertebral bone to provide superior bone fixation. In another embodiment, a bone anchor is placed through the pedicle of the inferior vertebra, across the disc space above the inferior vertebra, and into the lower boney surface of the upper vertebral bone. The implant employs a fastener that can be placed as free-standing device, or it can then be anchored to or interconnected with a fixation device that is anchored onto at least one spinous process. Further, a fastener may be used in this way through each of the two pedicles that are located on each side of the vertebral midline.

In another embodiment, an implant or orthopedic device is adapted to fixate the spinous processes of vertebral bones. The implant includes at least one bone engagement or abutment member located on each side of a spinous process of a first vertebra and a second vertebra, wherein the abutment members are adapted to forcibly abut the side of each spinous process. The implant has a locking mechanism that is adapted to rigidly immobilize at least a first abutment member on one side of the spinous process with at least a second abutment member on the other side of the spinous process (i.e., across the vertebral midline in the mid-sagittal plane from the first abutment member) using an interconnecting member (such as, for example, a rod, plate, etc) that crosses the vertebral midline. The locking mechanism is capable of reversibly transitioning between a first state, wherein the orientation between at least one abutment member and the interconnecting member is changeable in at least one plane and a second state, wherein the orientation between at least one abutment member and the interconnecting member is rigidly affixed. The implant further includes a compartment within at least one abutment member that is adapted to contain bone graft material, which can be bone graft, bone graft substitute, or a combination thereof.

In an aspect, there is disclosed an orthopedic implant for the fusion of adjacent bony segment. The implant comprises a first member and a second member opposed to the first member, wherein the first and second member define a space therebetween sized to receive a bone. The first and second members have opposed surfaces each surface having at least one spiked protrusion for capturing a bone therebetween. At least one of the members defines an internal compartment adapted to contain a bone graft material, the compartment communicating with at least one bore hole in the at least one member for communicating the bone graft material with the captured bone. The bone graft material in the compartment extends from a first side of the first captured bone to a first side of a second captured bone, wherein the first side of the first and second captured bones are also the sides penetrated by the spike protrusions.

Multiple additional embodiments are described herein. Other features and advantages should be apparent from the following description of various embodiments, which illustrate, by way of example, the principles of the disclosed devices and methods.

BRIEF DESCRIPTION OF THE DRAWINGS

FIG. 1 illustrates perspective and orthogonal views of a pair of vertebral bones.

FIG. 4 shows the system in an exploded state

FIG. 5 shows various orthogonal views of an exemplary body member of the system.

FIG. 7 shows perspective views of a locking member of the system.

FIG. 8 show orthogonal views of the locking member.

FIGS. 9A and 9B shows an embodiment of the system including a rod with spherical ends.

FIG. 10 shows a method of implanting and using the system 105.

FIG. 12A shows an embodiment of an assembled bone screw assembly.

FIG. 12B shows the bone screw assembly in an exploded state.

DETAILED DESCRIPTION

In order to promote an understanding of the principals of the disclosure, reference is made to the drawings and the embodiments illustrated therein. Nevertheless, it will be understood that the drawings are illustrative and no limitation of the scope of the invention is thereby intended. Any such alterations and further modifications in the illustrated embodiments, and any such further applications of the principles of the invention as illustrated herein are contemplated as would normally occur to one of ordinary skill in the art.

FIG. 1 illustrates perspective and orthogonal views of a pair of vertebral bones. The vertebrae are represented schematically and those skilled in the art will appreciate that actual vertebral bones may contain features that are not depicted in FIG. 1.

Figure 2:
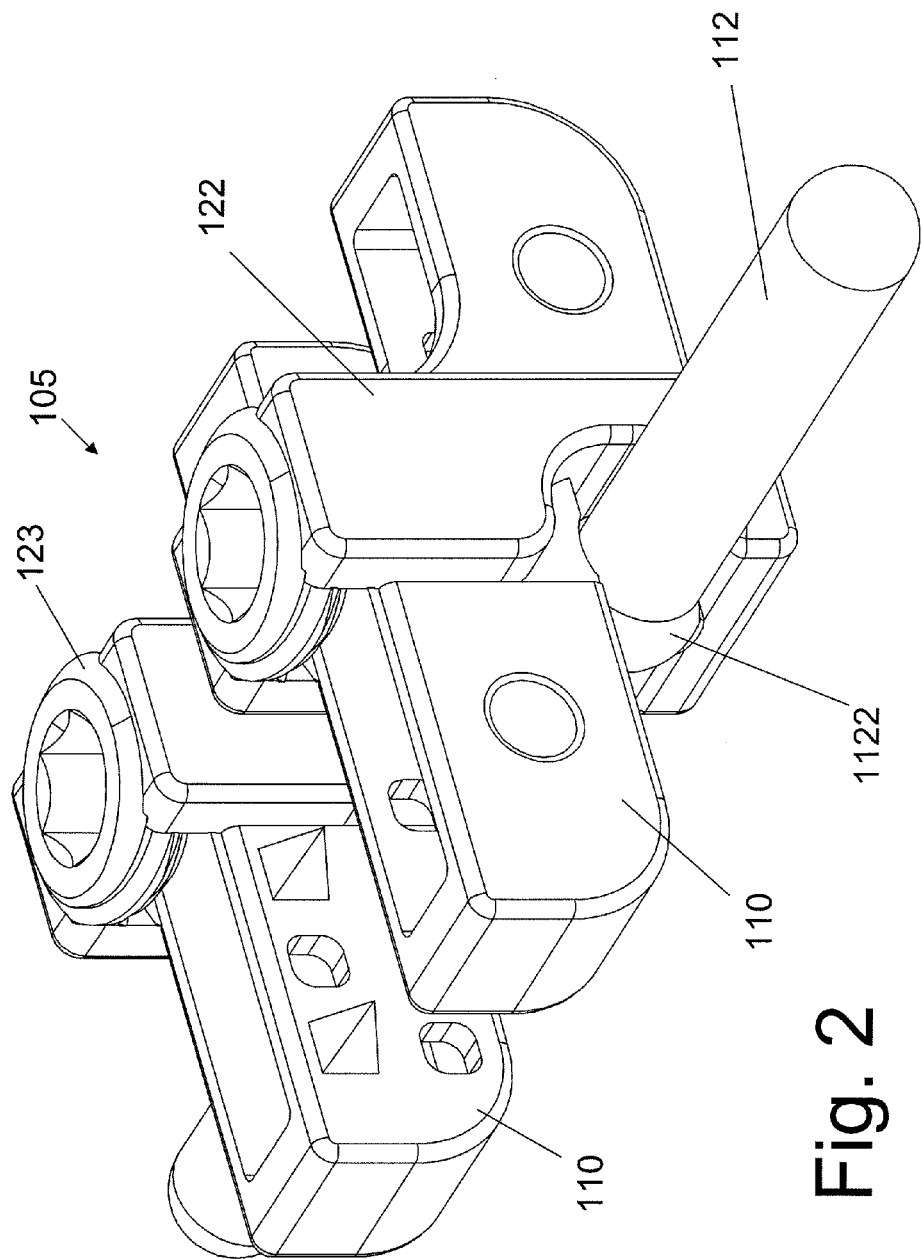
FIG. 2 shows a perspective view of a bone implant system in a completely assembled state

FIG. 2 shows a perspective view of a bone implant system 105 in an assembled state. The system 105 includes several components, including at least two body members 110 and an elongated interconnecting member, such as a rod 112 or plate, that interconnects the body members 110 in a spaced relationship with the space between the body members 110 sized and shaped to receive a portion of a vertebral body, such as a spinous process. (The system 105 is described herein in the exemplary context of being used with a rod 112 but it should be appreciated that a plate or other interconnecting member may be used in place of the rod 112.)

Figure 3:
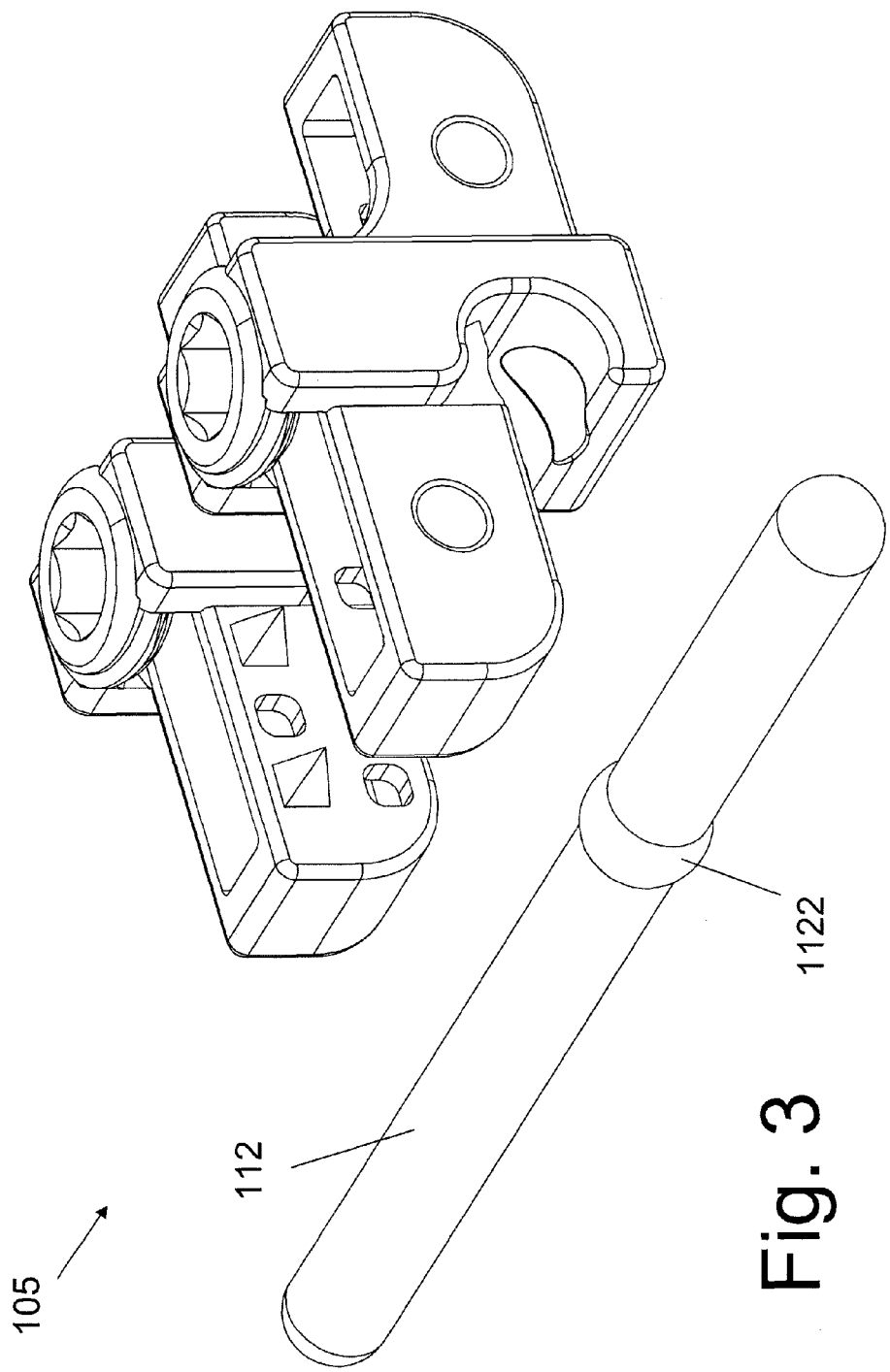
FIG. 3 shows the system with an interconnecting rod detached.

Each body member 110 has a corresponding locking member 122 that couples to the respective body member 110 as described below. In addition, each locking member 122 has a corresponding locking nut 123 that can be threaded onto the locking member 122 and used to apply a downward locking force onto the respective member 110 and the rod 112 to immobilize the member 110, rod 112, and locking member 122 relative to one another, as described more fully below. FIG. 3 shows the system 105 with the interconnecting rod 112 detached. FIG. 4 shows the system 105 in an exploded state. It should be appreciated that the use of terms herein such as "upward", "downward", "front" and "back" are with reference to the orientation shown in drawings and are not intended to be limiting.

Figure 6A:
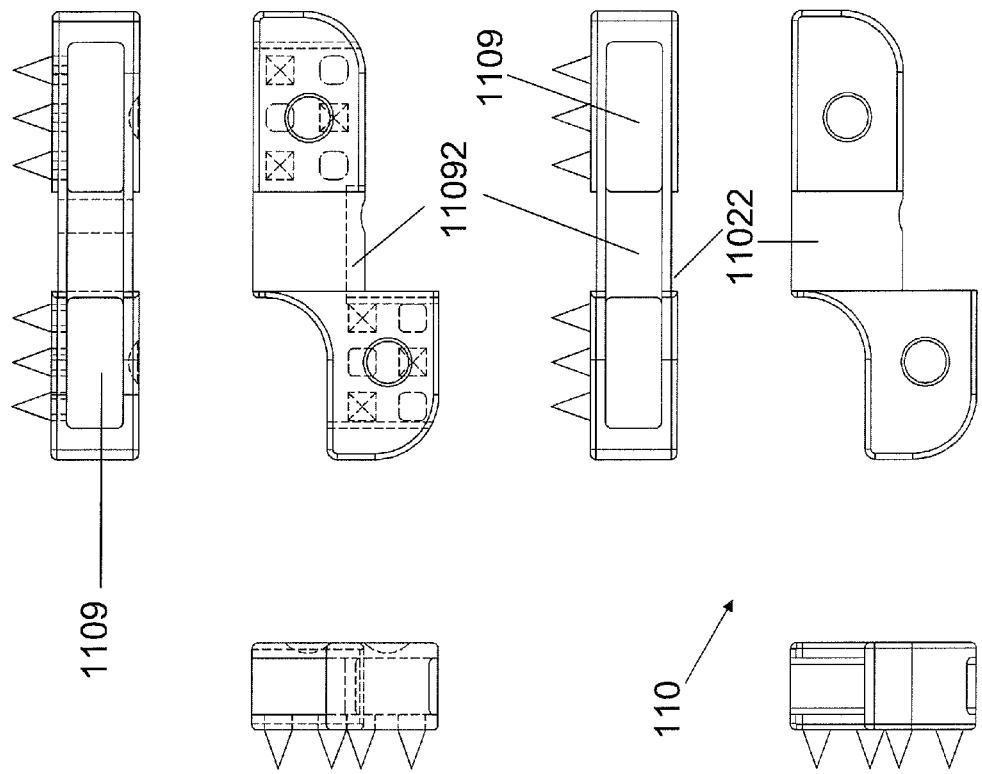
FIGS. 6A and 6B show plan views of the body member.
Figure 6B:
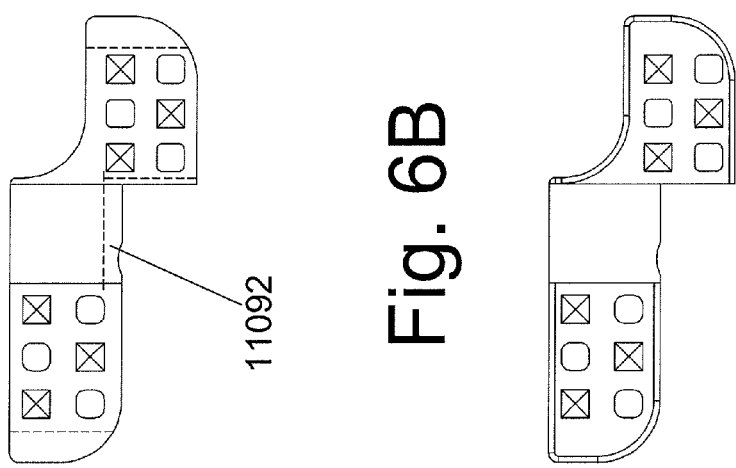

An exemplary embodiment of the body member 110 is now described with reference to FIG. 5 and FIGS. 6A and 6B. FIG. 5 shows various orthogonal views of the body member 110 while FIGS. 6A and 6B show plan views of the body member 110. FIG. 6A shows the body member 110 with internal lines and FIG. 6B shows the body member 110 without internal lines. The illustrated embodiment of the system 105 includes a pair of body members 110, each of which is a mirror image of the other.

With reference to FIGS. 5, 6A, and 6B, each body member 110 is an elongated body having outer walls that define a cavity that is at least partially enclosed by the outer walls. The body members are sized and shaped to be positioned next to and abut a spinous process of a vertebral body. In particular, each body member 110 includes a first side wall 1102, a second side wall 1104 opposed to the first side wall, a front wall 1106 and a back wall 1108 opposed to the front wall 1106. The walls 1102, 1104, 1106, and 1108 define an inner cavity 1109. The upper and lower boundaries of the inner cavity 1109 may be at least partially open, as depicted, or completely closed by additional walls. The cavity 1109 is adapted to open onto the space outside of member 110 through at least one aperture of the walls 1102, 1104, 1106, and/or 1108 and/or through the upper and lower boundaries of the cavity 109. That is, in an embodiment, the cavity 1109 is not a completely closed cavity. Thus, the walls 1102, 1104, 1106, and/or 1108 may include one or more holes, apertures, or openings that provide communication between the cavity 109 and a location outside of the body member 110.

The cavity 1109 is adapted to receive and contain a bone graft material (which can be bone graft, bone graft substitute, or a combination thereof) so that, when the system is implanted in the spine, the contained bone graft material can contact at least one vertebral bony surface through the aforementioned aperture of the walls or through the upper lower boundaries of the cavity 109 that surround cavity 1109. The bone graft material may then form a fusion mass with that bony surface.

With reference to FIG. 5 and FIG. 6B, the side wall 1102 of each body member 110 includes a channel 11022 that is sized and shaped to accept a corresponding locking member 122. The other side wall 1102 also includes a complementary channel 11042. The locking member 122 is sized and shaped so that it can be inserted onto a respective body member 110 over the channels 11022 and 11042 as shown in FIG. 2.

With reference still to FIGS. 5, 6A, and 6B, the wall 1102 includes one or more cut outs or seats 11024 sized and shaped to accept an instrument that can compress each of the two body members 110 toward and into the side bony aspect of a vertebral spinous process once the system 105 is coupled to a vertebral body. The seat 11024 does not necessarily extend through the full thickness of wall 1102.

The wall 1104 of each body member 110 includes one or more protrusions 11044 that are adapted to forcibly penetrate and fixate onto a bony surface of a vertebral bone onto which member 110 is forcibly applied. The protrusions have a shape, such as a pointed shape, that is configured to facilitate penetration into and fixation with the bony surface. One or more full thickness bore holes 11046 may extend through the wall 1104 of each body member 110 so that bone graft material contained in cavity 1109 can pass through the hole(s) 11046 and contact at least a portion of the vertebral bony surface that is in contact with the wall 1104 and thereby form a fusion mass with the vertebral bone.

As mentioned, the upper and lower boundaries of the cavity 1109 may be at least partially open (as shown in FIG. 5). The open upper and lower boundaries provide access to the cavity 109 to facilitate the placement of the bone graft material into cavity 1109. The open upper and lower boundaries may also serve as means through which bone graft material contained in cavity 1109 may come into contact with the adjacent vertebral bone. Further, in an embodiment, either the upper and/or lower boundaries of the cavity 1109 may contain a closed portion that encloses the upper or lower boundary. For example, the body member 110 may include a lower wall 11092 (FIG. 6B) that entirely or at least partially encloses the lower boundary of the cavity 1109 so as to limit contact between the graft material contained in cavity 1109 and structures that are preferably protected from bone graft contact. Such structures may include the dural surface of the spinal nerve column or spinal nerve. The lower wall 11092 may serve other functions, as discussed more fully bellow.

An exemplary embodiment of a locking member 122 is now described with reference to FIGS. 7 and 8. Each locking member has a pair of opposed, upwardly extending side walls 1222 that form a space therebetween. The space between the side walls is sized and shaped to complement the shape of the channels 11022 and 11042 on the body member 110. In this manner, the locking member 122 can be slid or otherwise coupled onto a corresponding body member 110 in the region of the channels 11022 and 11042. The region of the locking member 122 below the side walls 1222 includes a protrusion 1226 that is contoured or shaped to form a seat that is sized and shaped to receive the rod 112, as described more fully below. The seat has a rounded surface that may complement the shape of the rod 112 so that the rod 112 can be firmly seated onto the seat. In addition, the lower region of the side walls 1222 form ledges that overhang the seat.

The ledges and protrusion 1226 collectively form a space/seat in which the interconnecting rod can be captured and/or immobilized relative to the locking member 1222. The protrusion 1226 may include one more features adapted to accept a spherical portion of the interconnecting rod. For example, an indentation 12262 may be positioned on the protrusion for receiving a spherical portion of the interconnecting rod. The indentation may be sized and shaped to receive any of a variety of shaped portions of the rod not limited to a spherical portion.

With reference to FIG. 7, the interior surface of the side walls 1222 may have threads 1224 that threadingly mate with a corresponding locking nut 123. This permits the locking nut 123 to be threaded downward into the space between the side walls 1222.

The assembled system 105 is now further described with reference to FIG. 2. The two body members 122 are positioned in a spaced apart relationship and coupled to one another via the rod 112. That is, the rod 112 is seated onto the seats formed by the protrusions 1226 on the lower portion of the locking members 122. Each of the locking members 122 is positioned on a respective body member 110 such as over the channels 11042 and 11022 (FIG. 5). Thus, the locking members 122 are attached to the body members while the rod 112 is seated on the locking members 122 such that a space is defined between the body members 110 to collectively form the system 105.

The body members 110, locking members 122, and rod 112 can all be locked and immobilized relative to one another using the locking nuts 123. In particular, each locking nut is advanced downward into a locking member 122 such that the locking nut provides a downward force onto the body member 110, at least a portion of which is positioned between the locking nut 123 and rod 112. With downward advancement of nut 123, a lower or an inferior surface of the locking nut 123 is moved toward, and forced against, the upper edge(s) of the respective body member 110. The upper edge(s) may include each of the first side wall 1102 and/or the second side wall 1104.

The locking member 122 is thus forced upward relative to member 110 and the interconnecting rod 112 is forcibly constrained between ledge 1226 of the locking member 122 and the surface of the lower wall 11092 (FIG. 6A, 6B) of the cavity 1109. In this way, each of the body members 110 is immobilized relative to the interconnecting rod.

While rod 112 is depicted as having a spherical portion 1122 in FIGS. 2-3, a rod having a spherical end (as shown in FIGS. 9A-9B) may be alternatively used. Further, a straight or curvilinear rod without a spherical protrusion, a plate, or an interconnecting member of any applicable geometric configuration may be alternatively used to interconnect the body members 110. As can be seen in FIGS. 2 and 9A-9B, the spherical portion of rod 112 interacts with the indentation 12262 in the seat of locking member 122 and also with the lower surface of the wall 11092 of the member 110. This interaction allows the interconnecting rod 112 to be oriented and fixed in any one of a variety of positions (including non-orthogonal positions) relative to the body member 110 to which it is attached.

FIG. 10 shows a method of implanting and using the system 105. In use, the system is positioned posterior to the spinous processes, SP1 and SP2, of the vertebral bones to be immobilized. (Note that in FIG. 10, the system 105 is positioned above the posterior aspect of the vertebral bones. Thus, the system 105 is actually shown in a position that is anatomically posterior to the vertebral spinous processes, SP1 and SP2.) At this point in the implantation of the system 105, each of the locking nuts 123 is sufficiently loose so that each body member 110 can move relative to the interconnecting member 112. The system 105 is then moved so that each body member 110 rests adjacent to a side of each of the spinous processes SP1 and SP2 of the two vertebral bones to be immobilized. That is, the body members will be positioned on either side of at least one spinous process such that a spinous process is positioned between a pair of body members 110. Each body member 110 is then forced towards (that is, medial) the spinous processes positioned between the body members so that the protrusions 11044 of each second side wall 1104 of each body member 110 is forced into the side of the spinous process that is adjacent to it. In other words, the body members 110 are forced toward one another and also toward the spinous processes positioned between the body members 110 such that the protrusions penetrate the sides of the spinous processes.

Figure 11:
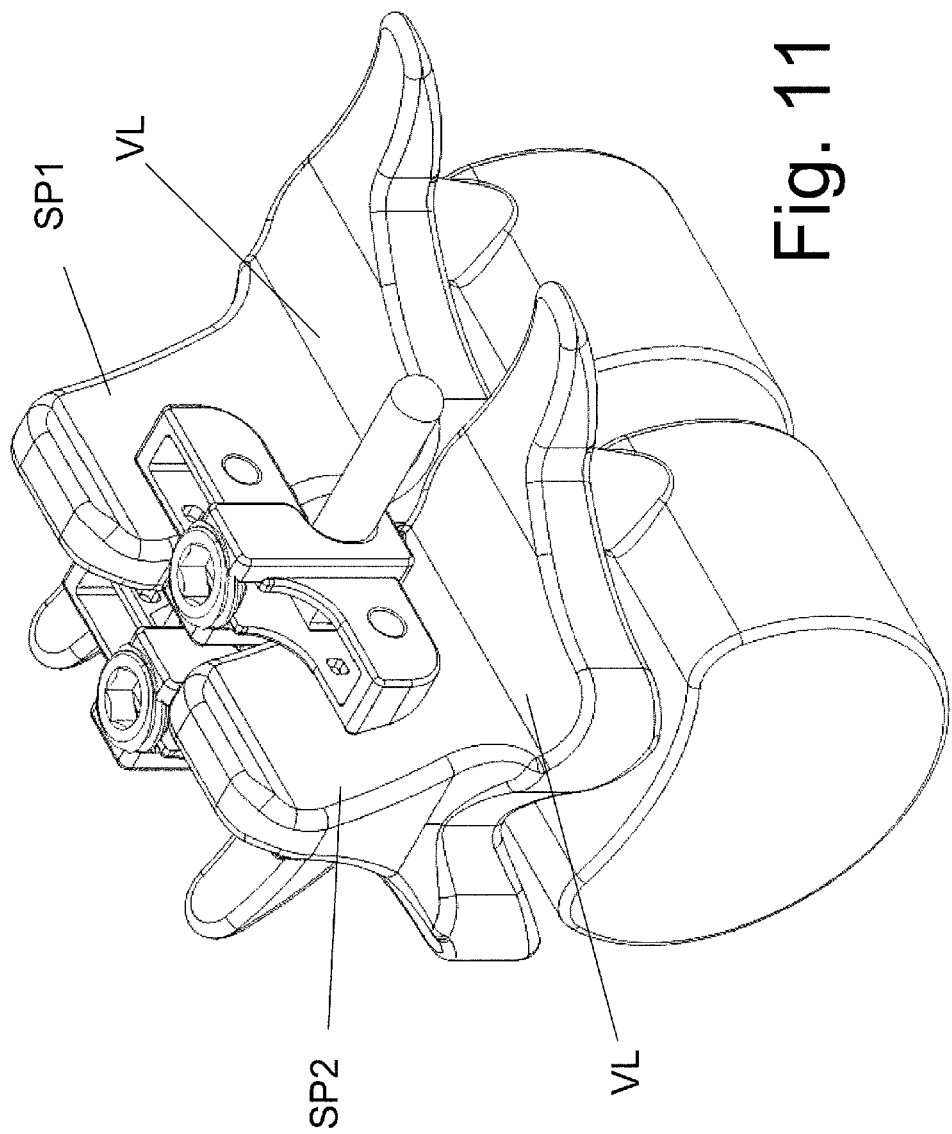
FIG. 11 shows the system in an implanted state.

The body members 110 are forced towards one another by the action of at least one driver instrument (in an embodiment, the driver instrument may be shaped like pliers) that is preferably adapted to interact with and compress each body member 110 toward one another. The driver instrument may interact with at, at least, one of indentations/cut outs 11024 of side wall 1102 of each body member 110. While at least one driver instrument maintains compression across the opposing body members 110 (and maintain a force that pushes the body members 110 toward one another), each of the locking nuts 123 is advanced downward toward the body members, as described above. The locking nuts 123 are advanced until all members (body member 110, locking member 122, and rod 112) of the system 105 are immobilized relative to one another. The driver instrument(s) is removed and each cavity 1109 (of the body members 110) is packed with bone graft material. Note that the bone graft material is then be placed in contact with the lateral wall of the spinous process, or forced out the lower surface of cavity 1109 and placed into contact with the posterior aspect of the vertebral lamina (VL), or both. (In the implanted state, the vertebral lamina are situated anatomically anterior to the implant.) The implanted system is shown in FIG. 11.

There is now described an additional embodiment wherein a bone screw assembly may be anchored into the pedicle portion of the vertebral bone and used as an additional point of device fixation. FIG. 12A shows an embodiment of an assembled bone screw assembly. FIG. 12B shows the bone screw assembly in an exploded state. The illustrated screw assembly is for example and those of ordinary skill in the art will appreciate that a large number of bone screws that are presently known, and/or yet to be known, may be alternative used in this application.

With reference to FIGS. 12A and 12B, the exemplary embodiment of the bone screw assembly includes a bone screw having a head and a shank. The head of the bone screw can be seated in a receiver assembly of the bone screw assembly. The receiver assembly includes an outer housing and an inner housing that collectively form a seat for the head of the bone screw. The bone screw assembly further includes a locking nut assembly that includes an upper member that is positioned above the head of the bone screw, a washer member and a locking nut. The upper member has a pair of outwardly extending arms that fit between upwardly extending prongs of the inner and outer housings of the housing assembly.

Figure 13A:
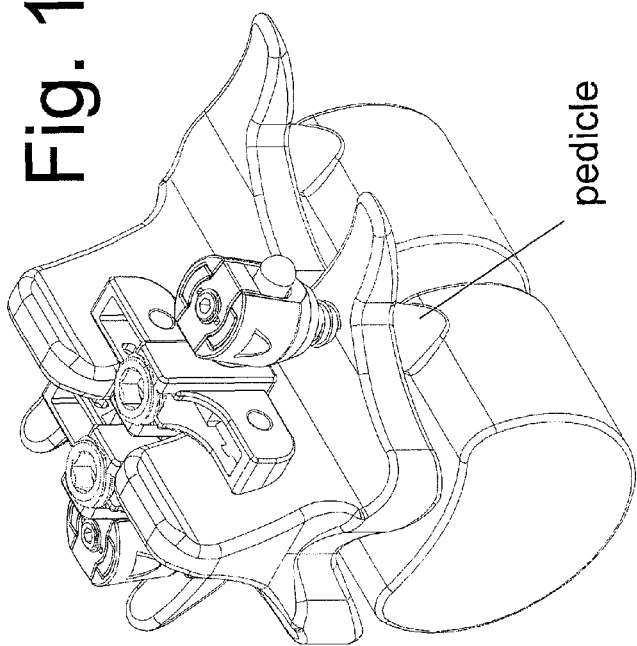
FIGS. 13A, 13B, 14, and 15 show a method and device for using the bone implant system with one or more bone screw assemblies.
Figure 13B:
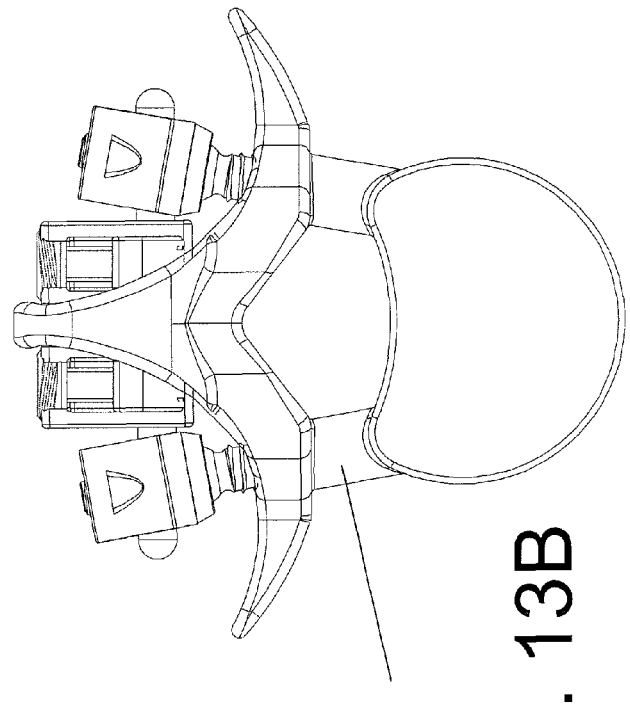

In use, with reference to FIG. 13A and FIG. 13B, at lease one bone screw assembly is placed into a pedicle portion of the vertebral bone. A screw assembly may be placed into the pedicle portion of each of the two pedicles of the lower (i.e., inferior) vertebral bone of the pair of vertebrae to be immobilized. In use, each bone screw may be positioned into the pedicle portion of the vertebral bones using any trajectory that permits proper screw placement. In a preferred embodiment, at least one bone screw is placed into the pedicle portion of the lower vertebral bone through a bone entry point that rests immediately inferior to the inferior articulating process of the upper (i.e., superior) vertebral bone of the pair of vertebrae to be immobilized. In this way, the inferior articulating process of the upper vertebral bone abuts the superior surface of the bone screw and prevents further extension of the upper vertebra relative to the lower vertebra. (Note that a facet joint is anatomically comprised of the articulation between the inferior articulating process (IAP) of an upper (superior) vertebral bone and the superior articulating process (SAP) of a lower (inferior) bone. These definitions of anatomical structures are known to those of ordinary skill in the art. They are described in more detail in *Atlas of Human Anatomy*, by Frank Netter, third edition, Icon Learning Systems, Teterboro, N.J. The text is hereby incorporated by reference in its entirety.)

Figure 14:
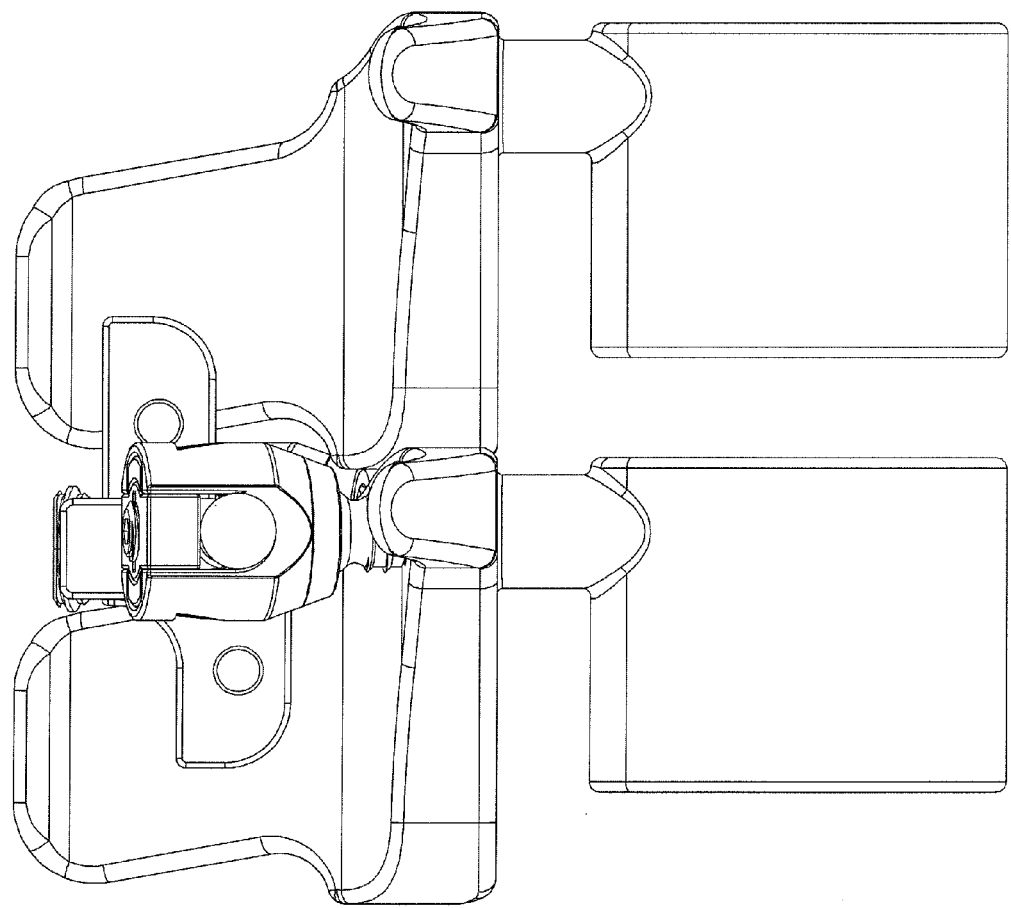

An elongated interconnecting rod is used to interconnect the screw assemblies. A system 105 is placed with body members 110 on each side of the spinous process (as described above) and coupled onto the rod as described above. (Alternatively, the interconnecting rod can be implanted with system 105 assembled and then lowered onto the screw assemblies.) After the placement of all instrumentation, the locking nuts 123 and the locking nut assembly 52 (shown in FIG. 12) of the bone screws assemblies are then locked and all members of the system 105 and bone screw assembly are immobilized. FIGS. 13 and 14 shown an assembled construct. This provides a significant increase in the immobilization power of the system 105.

Figure 15:
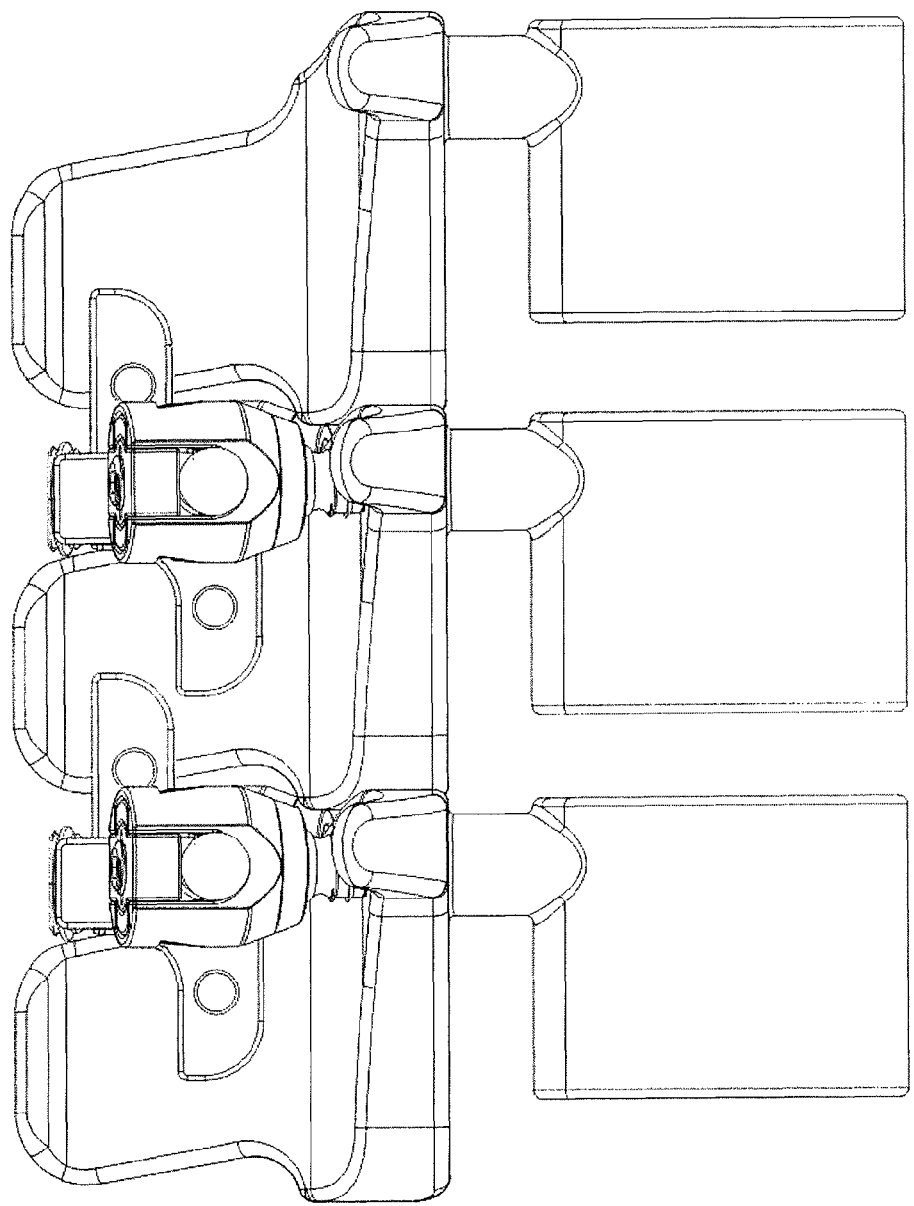

In another embodiment, multi-level fixation can be performed with serial implantation of multiple systems 105. The stepped configuration of each system 105 permits the placement of more than one system 105 on a single spinous process. FIG. 15 shows the fixation of three adjacent vertebral bones using two systems 105. While the systems 105 are shown attached to bone screws as in the embodiment of FIGS. 13 and 14, the systems 105 may be alternatively used without a bone screw anchor, as in the embodiment of FIG. 11.

Figure 16:
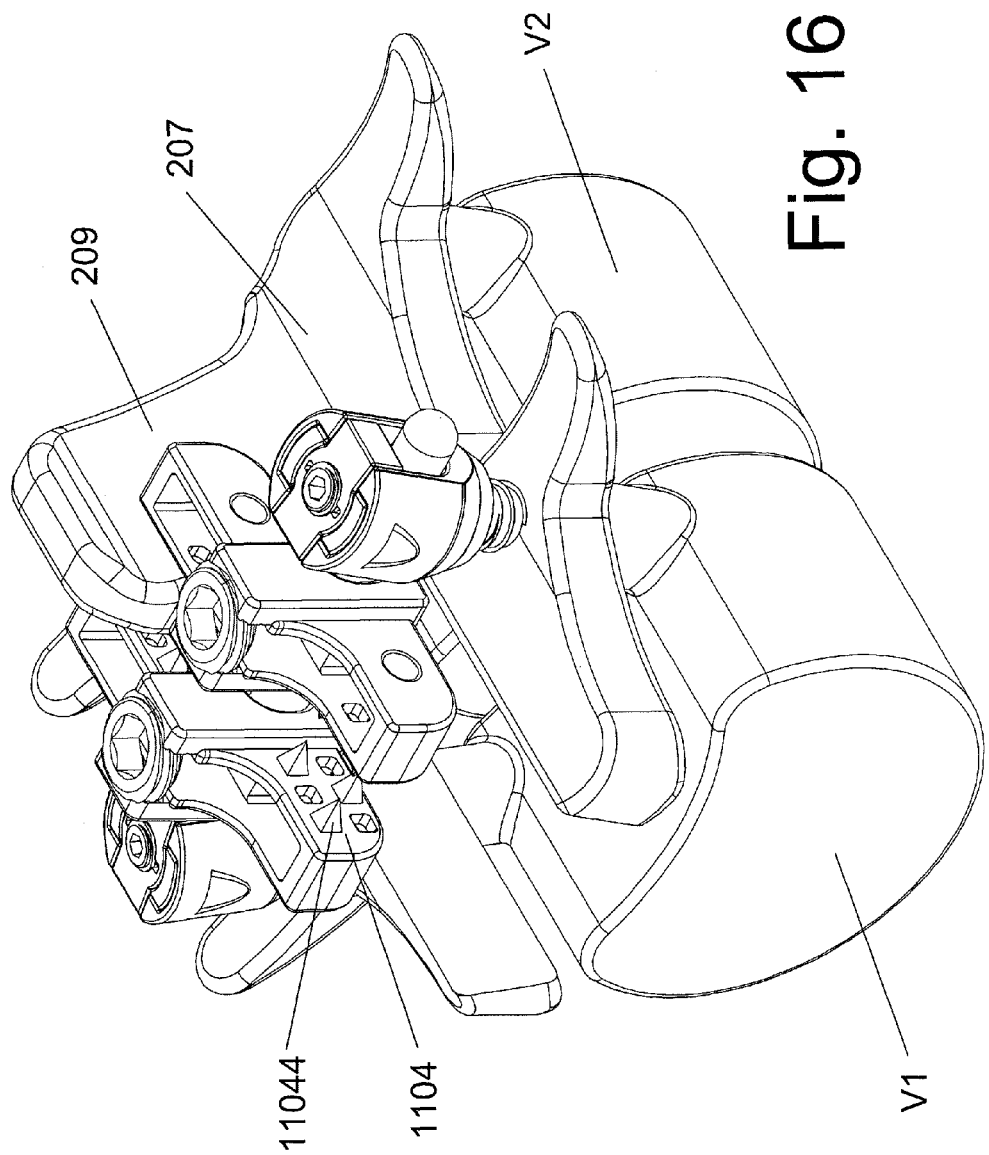
FIG. 16 shows use of the system wherein one vertebral bone does not have a spinous process that will permit device fixation.

FIG. 16 shows use of the system 105 wherein one vertebral bone does not have a spinous process that will permit device fixation. This situation can occur when, for example, the system 105 is used to immobilize the L5 and S1 vertebral bones. In that application, the S1 spinous process is often too small to accommodate the fixation of a portion of body member 110. In an additional embodiment, the situation can also arise when one of the vertebral bones had undergone a prior laminectomy. In either situation, the system 105 placed such that the body members 110 are affixed to the spinous process of a first vertebra and the pedicle portion of a second vertebra, wherein the attachment to the pedicles is preferably performed through the use of pedicle bone screws. That is, the system 105 is attached to pedicle screws via the rod 112.

By way of illustration, FIG. 16 shows that the lamina and spinous process of the inferior vertebra bone V1 have been removed. The lamina 207 and spinous process 209 of the upper vertebra V2 remains intact. While the protrusions 11044 of each body member 110 over the inferior vertebra bone V1 are shown as not contacting one another, in actual application the protrusions 11044 from each body member 110 over the removed lamina may abut at least a portion of the wall 1104 of the other member 110.

Figure 17A:
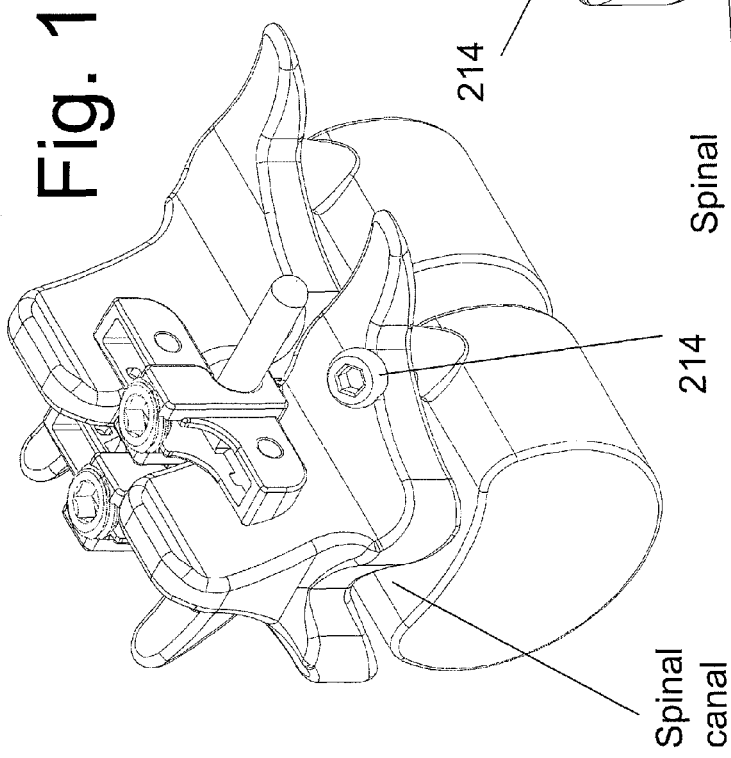
FIGS. 17A and 17B show an additional embodiment of the system 105 that may be used with a bone screw.
Figure 17B:
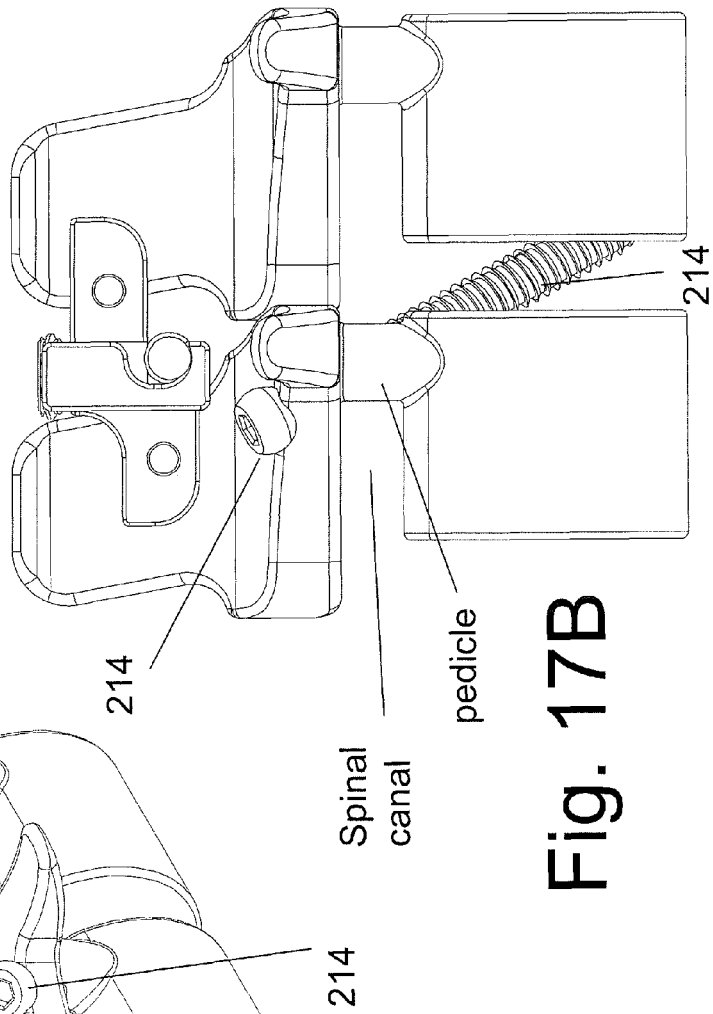

FIGS. 17A and 17B show an additional embodiment of the system 105 that may be used with a bone screw. In this embodiment, the bone screw 214 transverse the pedicle portion of a first vertebral bone, crosses the disc space between the first and second vertebral bones and enters the inferior surface of the second vertebral bone. While the bone screw is shown being detached from the system 105, it may be alternatively comprised of a bone screw assembly that can fixate onto the interconnecting rod (similar to the embodiments of FIGS. 13 and 14).

As shown in FIGS. 17A and 17B, a bone screw is used to cross the disc space and fixate the two vertebral bones. This fixation compliments the posterior fixation provided by the system 105 and thus provides fixation of the two vertebral bones that is both anterior and posterior to the spinal canal.

In an alternative embodiment, a fastener or bone screw may be similarly positioned into the pedicle of the inferior vertebra. The fastener then transverses the pedicle, crosses the disc space between the two vertebrae and enters the inferior aspect of the upper vertebra. The fastener may be further adapted to move the top vertebral bone relative to the lower vertebral bone. After re-positioning of the two vertebral bones, a system 105 may be then applied to the posterior aspect of the two vertebrae. These devices and methods of use are particularly useful to re-align, at least partially, vertebral bones that may be mal-aligned.

Figure 18:
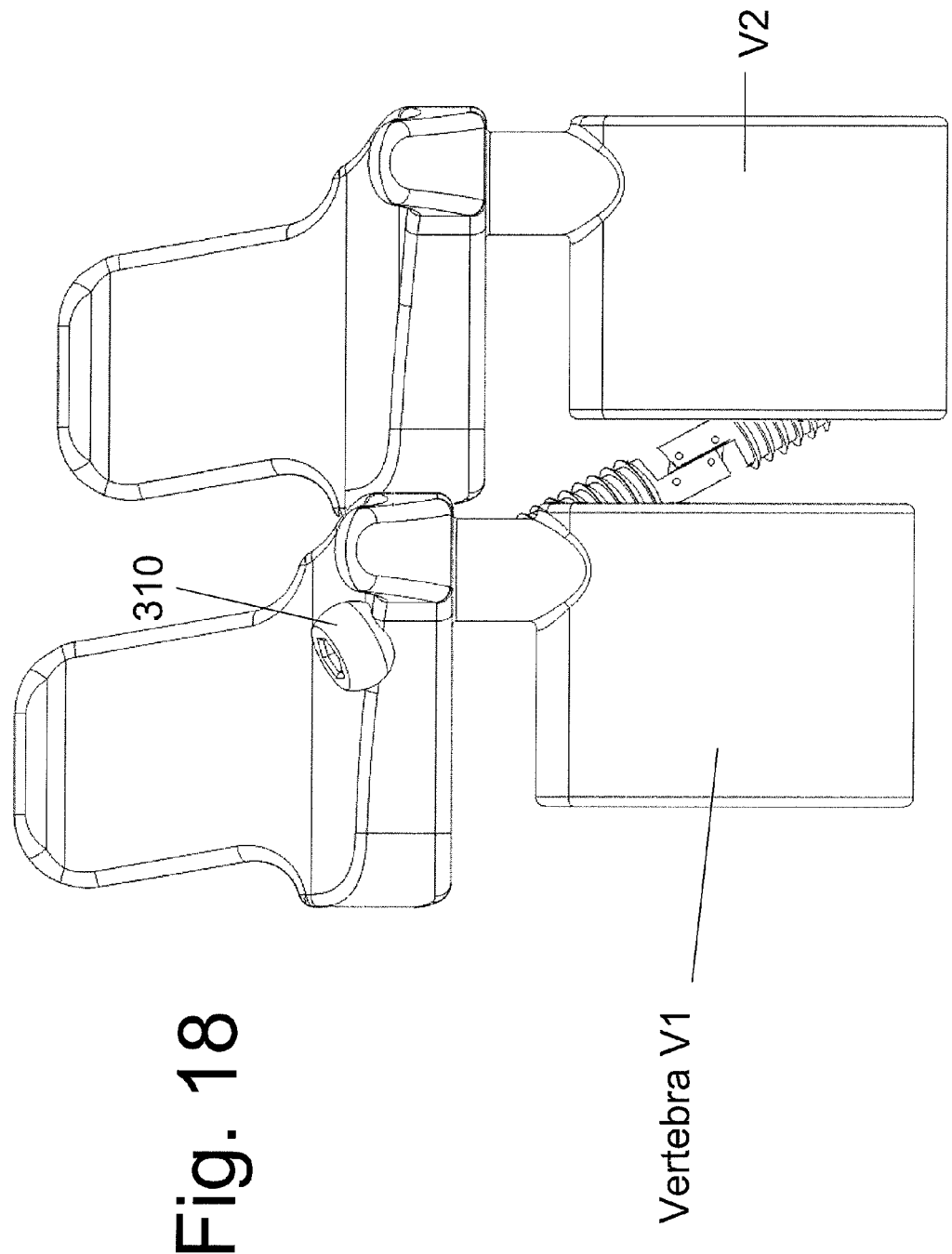
FIG. 18 illustrates an embodiment wherein a fastener is positioned through the pedicle of the inferior vertebra V1, across the disc space between the two vertebrae and into the inferior aspect of the upper vertebra.
Figure 19:
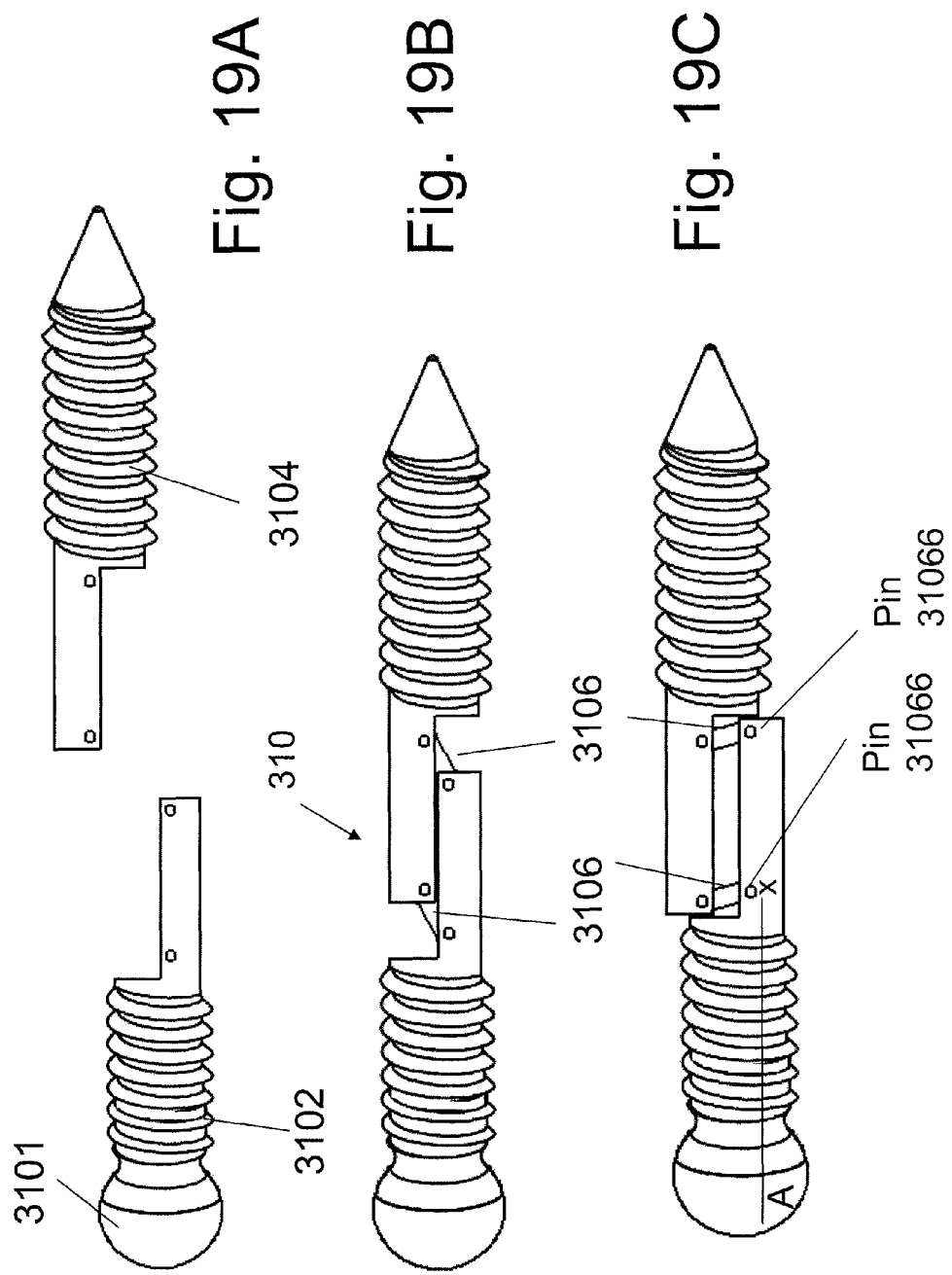
FIGS. 19A-19C show an exemplary embodiment of the fastener of FIG. 18.

FIG. 18 illustrates an embodiment wherein a bone screw or fastener 310 is positioned through the pedicle of the inferior vertebra V1, across the disc space between the two vertebrae and into the inferior aspect of the upper vertebra. FIG. 19A shows an exemplary embodiment of the fastener 310. The fastener includes a first threaded elongated segment 3102 and a second threaded elongated segment 3104 that are attached to one another in an assembled state. FIG. 19B shows an assembled fastener wherein the two device segments 3102 and 3104 are attached with at least one link member 3106. The link members 3106 are elongated members that attach at opposite ends to the device segments 3102 and 3104 in a pivoting manner. The fastener 310 is implanted while in the configuration depicted in FIG. 19B. In this configuration, the link members 3106 are pivoted outward such that the segments 3102 and 3104 are moved further away from one another. After placement, the fastener is transitioned into the configuration shown in FIG. 19C wherein the link members 3106 are pivoted inward such that the segments 3102 and 3104 are moved toward away one another. The instrumentation needed to place the fastener into bone is not shown, but may be a simple driver that engages head 3101. While not shown, the mechanism and/or instrumentation needed to transition the fastener from the configuration of FIG. 19B into the configuration of FIG. 19C may include any of the mechanism/instruments known in the art movement of a member 3104 relative to a member 3102. For example, it is contemplated that a small internal threaded screw is positioned within proximal member 3102. The engagable head of the small internal screw rests within head 3101 and the internal screw has a trajectory within the interior of the screw 310 that is eccentrically positioned along the long axis of member 3102. The trajectory of the small internal screw is schematically shown by A in FIG. 19C. To transition the screw 310 from the embodiment of FIG. 19B to the embodiment of FIG. 19C, the small screw is engaged and threadedly advanced so as to forcibly abut the member 3106 within the interior of screw 310 at or about point X (FIG. 19C). With advancement of the small internal screw, member 3106 is forcibly rotated about a fixation pin 31066.

Figure 20:
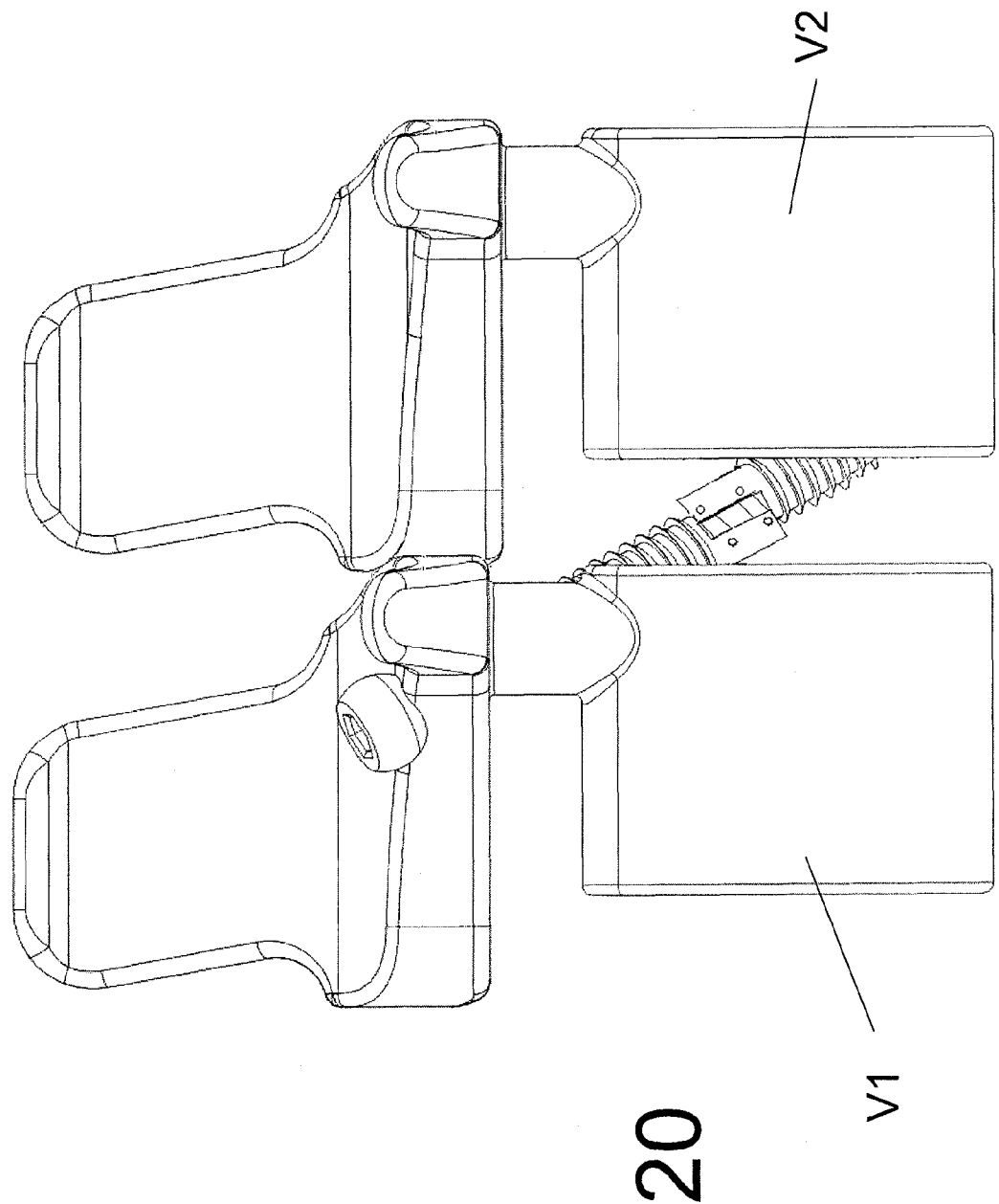
FIG. 20 shows the fastener in an implanted state.
Figure 21:
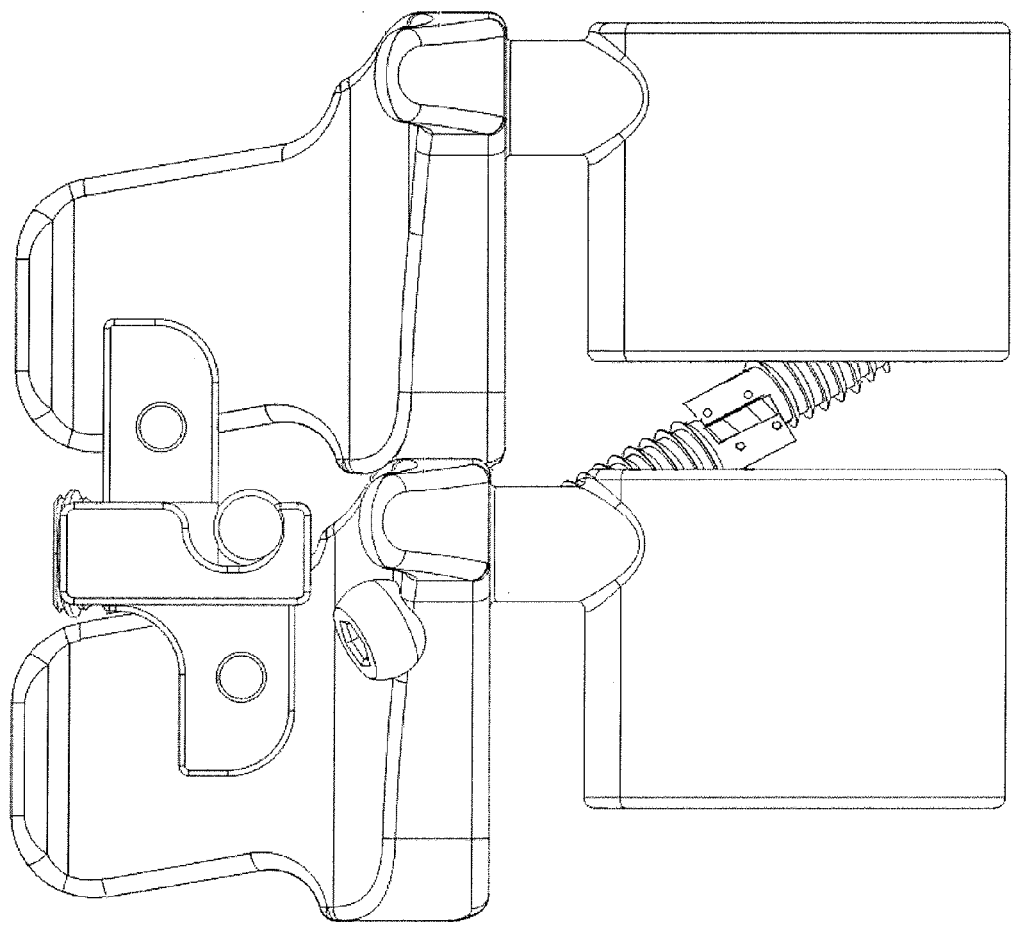
FIG. 21 shows the fastener and the system in an implanted state.

FIG. 20 illustrates how, with transition to the configuration of FIG. 19C, the fastener 310 can produce the posterior movement of the upper vertebra V2, as well as an increase in the distance between the vertebra across the disc space. The fastener can also produce an increase in segmental lordosis, wherein the lordotic curvature of the lumbar spine is reformed, with a change to the configuration of FIG. 19C. While the link members 3106 are shown as being substantially equal in length, they may alternatively be non-equal so at produce desired movement of the bones (such as additional lordosis) with configuration change of the fastener. After reducing the bones as shown in FIG. 20, the system 105 may be attached to the spinous processes of the vertebral bones in order to immobilize the vertebrae in this position. This is shown in FIG. 21. While bone screw 310 is illustrated as a singular bone screw with the movable feature discussed above, it may alternatively contain a proximal housing assembly that is adapted to accept an interconnecting rod. A example of a screw assembly is shown in FIG. 12. The illustrated screw assembly is for example and those of ordinary skill in the art will appreciate that a large number of bone screws that are presently known, and/or yet to be known, may be alternative used in this application.

The disclosed devices or any of their components can be made of any biologically adaptable or compatible materials. Materials considered acceptable for biological implantation are well known and include, but are not limited to, stainless steel, titanium, tantalum, shape memory alloys, combination metallic alloys, various plastics, resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible.

Therefore the spirit and scope of the appended claims should not be limited to the description of the embodiments contained herein.

The invention claimed is:

1. An orthopedic implant configured to attach to at least a first bone, comprising:
 a first body comprising:
  a first wall;
  a second wall;
  at least one connecting wall configured to join said first and second walls;
  at least one cavity formed by a separation of said first and second walls, said at least one cavity configured to house a bone forming material;
 a second body;
 an interconnecting member configured to movably couple said first body and said second body; and
 a locking mechanism comprising an unlocked state and a locked state, said locked state causing limited movement between said interconnecting member and at least one of said first and second bodies;
 wherein a superior surface of said first body comprises an aperture oriented to permit passage of said bone forming material into said at least one cavity when a bone abutment surface of said first body is positioned to abut said first bone.

2. The orthopedic implant of claim 1, wherein said first wall of said first body comprises at least a first side surface, and said second wall of said first body comprises an opposing second side surface, said first and second side surfaces configured to form at least a portion of a perimeter of said cavity.

3. The orthopedic implant of claim 2, wherein at least a portion of said cavity extends from a superior surface to an inferior surface in a vertical direction and from said first side surface of said first wall to said opposing second side surface of said second wall in a horizontal direction.

4. The orthopedic implant of claim 3, wherein said first wall comprises at least one bore hole configured to extend from said first to said second side surface.

5. The orthopedic implant of claim 1, wherein said second body comprises a first and a second end, at least one of said first and second ends comprising a side wall comprising a bone abutment surface; and wherein said bone abutment surface of said second body is substantially aligned to face said bone abutment surface of said first body.

6. The orthopedic implant of claim 5, wherein said bone abutment surface of at least one of said first and second bodies comprises at least one protrusion configured to fixate onto said first bone.

7. The orthopedic implant of claim 1, wherein said cavity comprises an aperture sized to permit passage of a bone forming material therethrough when said bone abutment surface of said first body is positioned to abut said first bone.

8. The orthopedic implant of claim 7, wherein said aperture is sized to permit formation of a fusion mass with a lamina portion of said first bone.

9. An orthopedic implant configured to fixate a first vertebral bone and a second vertebral bone, comprising:
 a first body comprising:
  a first wall, at least partially comprising a bone abutment surface configured to abut at least one of said first and second vertebral bones;
  a second wall;
  at least one connecting wall configured to join said first and second walls; and
  a cavity configured to comprise a bone forming material, said cavity being formed at least by said first wall, said second wall, and said at least one connecting wall;
 a second body comprising at least bone abutment surface adapted to abut each of said first and second vertebral bones, said bone abutment surface of said second body being substantially aligned so as to face said bone abutment surface of said first body;
 an interconnecting member configured to movably couple said first and said second bodies; and
 at least one locking feature configured to transition to a locked state, said locked state configured to limit movement of said first body in a direction away from said second body;
 wherein:
  said bone abutment surface of said first body is configured to extend along a horizontal axis for a distance greater than said connecting wall; and
  one or more bore holes of said cavity are sized to permit passage of a bone forming material therethrough after implantation of said orthopedic device.

10. The orthopedic implant of claim 9, wherein said first wall and said connecting wall are non-separable.

11. The orthopedic implant of claim 9, wherein said bone abutment surfaces of said first and second bodies comprise at least one protrusion configured to fixate onto at least one of said first and second vertebral bones.

12. The orthopedic implant of claim 9, wherein said one or more bore holes further enable formation of a fusion mass.

13. The orthopedic implant of claim 9, wherein said locking feature is positioned at said segment of intersection between said interconnecting member and said first body.

14. The orthopedic implant of claim 9, wherein advancement of a threaded member transitions said locking feature from a first state wherein said first body is movable relative to said interconnecting member, to said locked state, said first body being substantially immobilized relative to said interconnecting member when said locking feature is in said locked state.

15. The orthopedic implant of claim 9, wherein said implant is at least partially manufactured from Titanium.

16. An orthopedic device configured to fixate a spinous process of a first vertebral bone to a spinous process of a second vertebral bone, comprising:
 a first member comprising:
  a first wall and a second wall, said first wall comprising a first side surface and an opposing second side surface, said first wall configured to extend substantially along a first horizontal axis and being attached to said second wall, said second wall configured to extend substantially along a second horizontal axis; and
  a cavity at least partially defined by said first side surface of said first wall and said second wall, said cavity configured to extend substantially along a vertical axis from
 a superior surface to an inferior surface;
 a second member configured to extend substantially along a longitudinal axis from a front end to a back end, and having a first side wall comprising a first bone abutment surface configured to abut a second contralateral side of said spinous processes of said first and said second vertebral bones; and
 an interconnecting member configured to couple said first and said second members;

wherein one or more surfaces of said cavity comprise one or more apertures sized to permit passage of a bone forming material therethrough after implantation of said orthopedic device.

17. The orthopedic device of claim 16, further comprising at least one movement restriction feature, said movement restriction feature configured to transition from an unlocked state to a restricted state, said restricted state causing movement between said interconnecting member and at least one of said first and second members to be limited.

18. The orthopedic device of claim 17, wherein said movement restriction feature transitions from said unlocked state to said restricted state via advancement of a threaded member into at least a portion thereof.

19. The orthopedic device of claim 16, wherein said second side surface of said first wall comprises a first bone abutment surface that is adapted to abut a first ipsilateral side of said spinous processes of each of said first and said second vertebral bones, and said bone abutment surfaces of each of said first and second members are substantially aligned to face one another.

20. The orthopedic device of claim 19, wherein said bone abutment surfaces of each of said first and second members comprise one or more features configured to fixate to said bone.

21. An orthopedic assembly for fixation of a first vertebral bone and a second vertebral bone, comprising:
  a first assembly comprising:
    a first member configured to extend from a first end thereof to a second end thereof and having a first side surface and an opposing second side surface, said first side surface comprising a bone abutment surface configured to abut a first ipsilateral side of said spinous processes of each of said first and said second vertebral bones;
    a second member configured to extend from a first end thereof to a second end thereof and having a first side surface and an opposing second side surface, said first side surface comprising a bone abutment surface configured to abut a second contralateral side of said spinous processes of said first and said second vertebral bones; and
    an interconnecting member configured to couple said first and said second members; and
  a fastener assembly comprising a fastener and a housing, said fastener configured to anchor to a pedicle portion of said first or said second vertebral bones, and said housing configured to couple to said fastener at a first segment thereof and seat said interconnecting member of said first assembly at a second segment thereof;
  wherein said bone abutment surface of each of said first and second members are substantially aligned to face one another; and
  wherein at least one of said first and second members further comprises a feature configured to limit movement between said first and second members.

* * * * *